US00PP17173P2

(12) United States Plant Patent
Jonkers

(10) Patent No.: US PP17,173 P2
(45) Date of Patent: Oct. 24, 2006

(54) *DIASCIA* PLANT NAMED 'DALA WHIT'

(50) Latin Name: *Diascia barberae*
Varietal Denomination: Dala Whit

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/269,170

(22) Filed: Nov. 8, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP14,782 P2 * 5/2004 Stemkens ..... Plt./263

OTHER PUBLICATIONS

UPOV ROM GTITM Computer Database, GTI Jouve Retrieval Software 2005/05 Citaitons for 'Dala Whit'.*

* cited by examiner

*Primary Examiner*—Wendy Haas
(74) *Attorney, Agent, or Firm*—Jondle & Associates P.C

(57) ABSTRACT

A new *Diascia* plant particularly distinguished by its pure white medium-sized flowers, relatively long and upright inflorescences, deep green foliage, narrow and pointed leaves, and narrow plant habit with mostly upright branches is disclosed.

1 Drawing Sheet

Genus and species: *Diascia barberae.*
Variety denomination: 'Dala Whit'.

BACKGROUND OF THE NEW PLANT

The present invention comprises a new and distinct cultivar of *Diascia*, botanically known as *Diascia barberae*, and hereinafter referred to by the cultivar name 'Dala Whit'. The new cultivar originated in 2003 in Andijk, The Netherlands from the self-pollination of 'DSZ-40-6' an unpatented rose-colored proprietary *Diascia* plant. The seeds produced by the self-pollination of 'DSZ-40-6' were sown in May 2003, and the resulting seedlings were selected in July 2003. A single plant selection was chosen for further evaluation and for asexual propagation in the fall of 2003.

The new cultivar was created in 2003 in Andijk, The Netherlands and has been asexually reproduced repeatedly by vegetative cuttings and tissue culture micropropagation in Andijk, The Netherlands over a two-year period. The plant has also been trialed at Gilroy, Calif., and Andijk, The Netherlands. The present invention has been found to retain its distinctive characteristics through successive asexual propagations.

Plant Breeder's Rights for this cultivar were applied for in Europe on Jan. 24, 2005 and in Canada on Jul. 19, 2005.

SUMMARY OF THE INVENTION

The following are the most outstanding and distinguishing characteristics of this new cultivar when grown under normal horticultural practices in Gilroy, Calif. and Andijk, The Netherlands.

1. Pure white, medium-sized flowers;
2. Relatively long and mostly upright inflorescences;
3. Deep green foliage with narrow pointed leaves;
4. Medium vigor with fair branching; and
5. Narrow plant habit with mostly upright branches.

DESCRIPTION OF PHOTOGRAPH

This new *Diascia* plant is illustrated by the accompanying photograph which shows blooms, buds, and foliage of the plant in full color; the colors shown are as true as can be reasonably obtained by conventional photographic procedures. The photograph is of three six-month-old plants grown in a greenhouse with natural light in spring trial setting.

The accompanying photograph shows blooms, buds, mature foliage, and plant habit; the inset shows mature inflorescences and buds.

DESCRIPTION OF THE NEW CULTIVAR

The following detailed descriptions set forth the distinctive characteristics of 'Dala Whit'. The data which define these characteristics were collected from asexual reproductions carried out in Hillscheid, Germany. The plant history was taken on seven-month-old plants grown, 3 plants each, in 35-cm-diameter baskets (capable of holding 5-liters of soil) in an outdoor trial field under poly-cover rain protection. Color readings were taken under natural light. Color references are primarily to The R.H.S. Colour Chart of The Royal Horticultural Society of London (R.H.S.) (2001 edition).

DESCRIPTION OF THE NEW PLANT

Classification:
*Family.*—Scrophulariaceae.
*Botanical name.*—*Diascia barberae* Hook.
Parentage: Self-pollination of 'DSZ-40-6' a proprietary *Diascia* plant (unpatented).
Growth:
*Form and habit.*—Upright and outwardly spreading.

*Growth and branching habit.*—Ascending and outwardly spreading and changing to freely branching with overhanging; pinching enhances branching.

*Height.*—28 cm (from top of soil) for 7-month-old plants to 33 cm (total vertical height) of a plant in a hanging basket.

*Width.*—55 cm for a 7-month-old plant.

*Spread* (*including flowers*).—48 cm, from the base of the main stem to the tips of the branches.

*Time to produce a finished flowering plant.*—10–11 weeks for a 5-inch pot.

*Outdoor plant performance.*—Plant in full sun; is free-flowering through the summer; has some heat tolerance; use in mixed container planting or mass planting in a bed.

*Time to initiate and develop roots.*—20 days.

*Root description.*—Fibrous and freely branching.

Leaves:

*Arrangement.*—Simple and opposite.

*Shape.*—Deltoid.

*Apex.*—Acute.

*Base.*—Truncate.

*Margin.*—Weakly serrate.

*Texture.*—Glabrous, smooth, and slightly glossy.

*Immature.*—Color: Upper surface: RHS 137D to RHS 143A. Lower surface: RHS 138B.

*Mature* (*fully expanded*).—Length: 1.5–1.7 cm. Width: 1.0 cm. Color: Upper surface: RHS 137A. Lower surface: RHS 138B.

*Venation.*—Type: Pinnate. Color: RHS 145A to RHS 145B.

*Petiole.*—Length: 0.2 cm. Width: 0.2 cm. Color: RHS 144A.

Stems:

*Length.*—About 35 cm without the inflorescence.

*Diameter.*—0.3 cm as measured in the middle (is square not round).

*Internode length.*—1.2–2.2 cm.

*Color.*—RHS 143A.

*Texture.*—Appears smooth and glabrous but there is sparse pubescence.

*Anthocyanin.*—Absent.

Flower bud:

*Shape.*—Roughly globular and somewhat flattened.

*Diameter.*—0.6 cm.

*Length.*—0.4 cm.

*Color* (*at tight bud*).—RHS 150D to RHS 155A.

Inflorescence:

*Inflorescence type.*—Terminal raceme with florets in an alternate arrangement.

*Blooming habit.*—Fairly continuous through the summer.

*Quantity of inflorescences per plant.*—85 per plant.

*Lastingness of individual blooms on the plant.*—3–4 days.

*Fragrance.*—None.

*Inflorescence length.*—About 14–16 cm.

*Penduncle.*—Color: RHS 143A. Length: 14.0–15.5 cm. Diameter: 0.2 cm or less. Texture: Finely pubescent.

Flower:

*Type.*—Single, zygomorphic; 5-lobes fused at the base with the lobes directed at nearly 180-degree angles.

*Quantity* (*per raceme*).—About 20–25 flowers and buds in various stages of development; most often 4 flowers open at the same time; flowers are solitary at a distance of 1.0–1.5 cm.

*Shape.*—Salver-shaped.

*Diameter.*—1.8–1.9 cm.

*Color.*—Upper surface: RHS 155D (pure white). Lower surface: RHS 155D. Corolla (inside color): RHS 155D; upper petals have a patch of RHS 11A (yellow).

*Petals* (*lobes*).—Quantity: 5. Arrangement: Two upper lobes (mainly fused) with two lateral lobes and one lower lobe. Apex: Rounded. Base: Fused. Margin: Entire. Texture: Papillose.

*Upper lobes, size.*—Length (from the Corolla opening): 0.5 cm. Width: 1.1 cm.

*Lateral lobes, size.*—Length (from the Corolla opening): 0.6 cm. Width: 0.8 cm. Spur: Shape: Narrow, funnel-shaped and directed downwards. Length: 0.7–0.8 cm. Diameter: 0.3 cm, at the petal. Color: RHS 155A (white).

*Lower lobe.*—Length (from the Corolla opening): 0.9–1.1 cm. Width: 1.3–1.6 cm.

*Sepals.*—Quantity: 5. Color: RHS 143A. Length: 0.2 cm. Width: Up to 0.1 cm. Shape: Deltoid to lanceolate. Apex: Acute. Base: Fused. Anthocyanin: Absent. Texture: Rough and covered with pubescence.

*Pedicels.*—Color: RHS 144B (light green). Length: 1.2–1.4 cm. Diameter: 0.1 cm. Texture: Pubescent.

Reproductive organs:

*Stamens.*—Quantity: 4; coherent and arching towards and somewhat twisting around the pistil. Filament: Color: RHS 155A to RHS 157D (white). Length: 0.3–0.4 cm. Diameter: 0.1 cm. Anther color: RHS 14D (light yellow). Pollen amount: Abundant. Pollen color: RHS 14A (yellow).

*Pistils.*—Quantity: 1. Length: 0.3–0.4 cm. Stigma color: RHS 143D. Style color: RHS 145C.

Fruit and seed set: Has not been observed.

Disease and insect resistance: Has not been observed.

COMPARISON WITH PARENTAL AND COMMERCIAL CULTIVARS

'Dala Whit' differs from the self-pollination parent, proprietary plant 'DSZ-40-6' (unpatented), in that 'Dala Whit' has a white flower color while 'DSZ-40-6' has a rose flower color. Additionally, 'Dala Whit' has smaller and darker leaves and a more vigorous growth habit than 'DSZ-40-6'.

'Dala Whit' differs from the commercial cultivar 'Diastara' (U.S. Plant Pat. No. 14,782) in that 'Dala Whit' has a pure white flower color while 'Diastara' has a blush flower color. Additionally, 'Dala Whit' has smaller and darker green leaves and has a less densely-branched plant habit than 'Diastara'.

I claim:

1. A new and distinct cultivar of *Diascia* plant as shown and described herein.

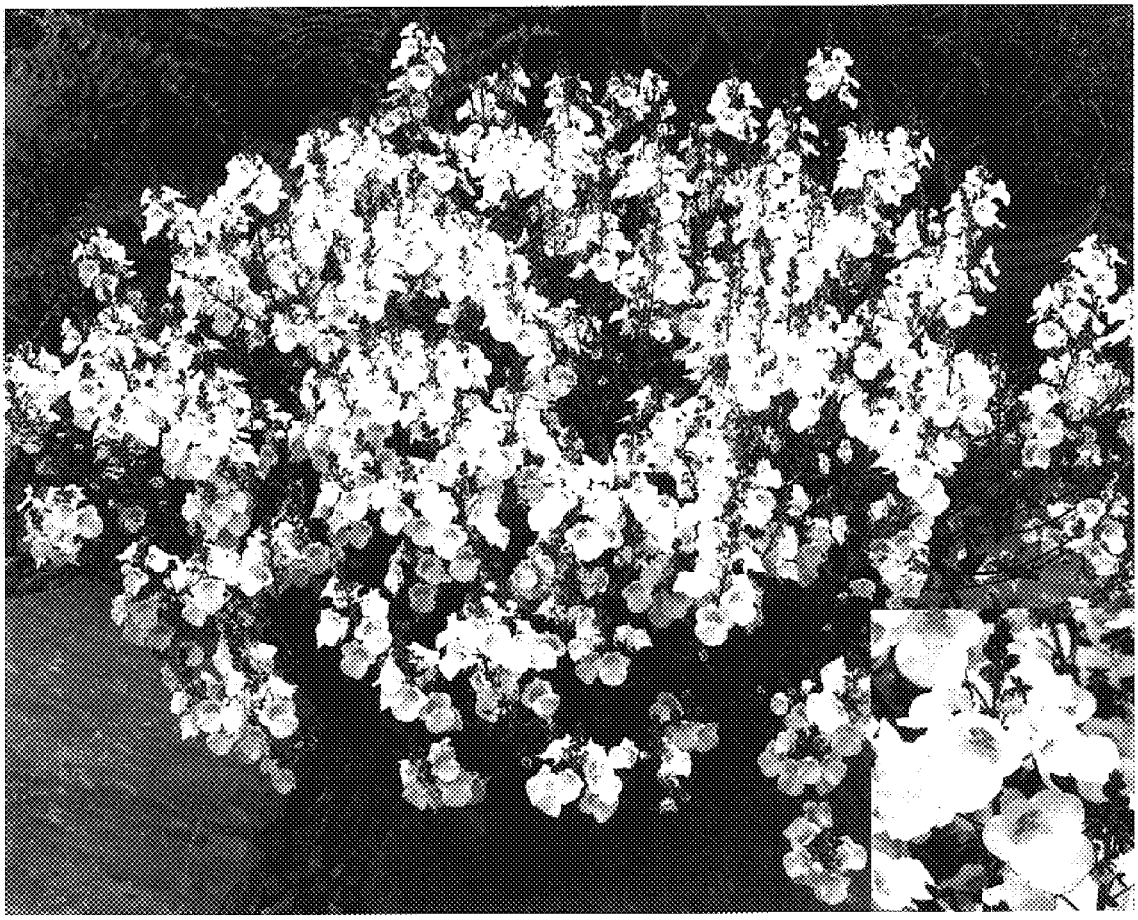

* * * * *